United States Patent
Kingsley

(10) Patent No.: US 9,302,006 B2
(45) Date of Patent: *Apr. 5, 2016

(54) SYSTEMS AND METHODS FOR TREATING FIBROMYALGIA

(75) Inventor: Joe D. Kingsley, Castle Valley, UT (US)

(73) Assignee: DMA International, Inc., Moab, UT (US)

( * ) Notice: Subject to any disclaimer, the term of this patent is extended or adjusted under 35 U.S.C. 154(b) by 681 days.

This patent is subject to a terminal disclaimer.

(21) Appl. No.: 13/603,183

(22) Filed: Sep. 4, 2012

(65) Prior Publication Data

US 2013/0236572 A1  Sep. 12, 2013

Related U.S. Application Data

(63) Continuation of application No. 12/484,567, filed on Jun. 15, 2009, now Pat. No. 8,257,752.

(51) Int. Cl.
| | |
|---|---|
| *A01N 65/00* | (2009.01) |
| *A61K 45/06* | (2006.01) |
| *A61K 36/00* | (2006.01) |
| *A61K 31/165* | (2006.01) |
| *A61K 36/73* | (2006.01) |
| *A61K 36/752* | (2006.01) |
| *A61K 36/82* | (2006.01) |
| *A61K 36/886* | (2006.01) |
| *A61K 36/185* | (2006.01) |
| *A61K 36/738* | (2006.01) |
| *A61K 36/88* | (2006.01) |

(52) U.S. Cl.
CPC .............. *A61K 45/06* (2013.01); *A61K 31/165* (2013.01); *A61K 36/00* (2013.01); *A61K 36/185* (2013.01); *A61K 36/73* (2013.01); *A61K 36/738* (2013.01); *A61K 36/752* (2013.01); *A61K 36/82* (2013.01); *A61K 36/88* (2013.01); *A61K 36/886* (2013.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 5,227,163 A | 7/1993 | Eini et al. |
| 5,411,992 A | 5/1995 | Eini et al. |
| 5,599,803 A | 2/1997 | Hainrihar et al. |
| 5,858,383 A | 1/1999 | Precopio |
| 5,902,595 A | 5/1999 | Burklow et al. |
| 6,160,724 A | 12/2000 | Kawada et al. |
| 6,350,724 B1 | 2/2002 | Kiel et al. |
| 6,607,716 B1 | 8/2003 | Smith et al. |
| 6,969,522 B2 | 11/2005 | Bessette |
| 6,974,584 B2 | 12/2005 | Bessette |
| 7,282,211 B2 | 10/2007 | Ping |
| 7,807,190 B2 | 10/2010 | Kingsley |
| 8,257,752 B2 | 9/2012 | Kingsley |
| 2004/0146587 A1 | 7/2004 | Spicer |
| 2007/0020304 A1 | 1/2007 | Tamarkin et al. |
| 2007/0077262 A1 | 4/2007 | Scialdone |
| 2008/0118585 A1 | 5/2008 | Nouvel |
| 2008/0145462 A1 | 6/2008 | Enan |
| 2009/0022826 A1 | 1/2009 | Shrier et al. |
| 2011/0065627 A1 | 3/2011 | Barathur et al. |

OTHER PUBLICATIONS

Rasatantrasarab Evam Siddhaprayogasamgrahah—part 1, 05 (p. No. 4-8) (Ref. p. No. of publication: 868-869), Publication Date—Edn 8th: 1990, Krishan Gopal Ayurveda Bhawan, Place of Publication—India.†

Kannusarny Pillai, Kannusamiyam Ennum Vaidhiya Sekaram, 05 (p. No. 9-13) (Ref. p. No. of publication:164), Publication Date—Edn: 7th.1963, B.Rathna Nayakar & sons, Thirumagal Achagam, Place of Publication—chennai, India.†

Mohammad Azam Khan, Ikseer Azam, vol. 1, 04 (p. No. 14-17) (Ref. p. No. of publication:71), Fourth Edition, Munshi Nawal Kishore, Place of Publication—Lucknow, India.†

† cited by third party

*Primary Examiner* — Michael Meller

(74) *Attorney, Agent, or Firm* — Kirton McConkie; David B. Tingey

(57) ABSTRACT

A solution and method for treating symptoms commonly associated with fibromyalgia. The solution includes a solvent and a composition including active ingredients of menthol, camphor, and capsaicin, as well as additional components including aloe vera extract, carbomer, decyl polyglucose, deionized water, grapefruit seed extract, green tea extract, orange peel extract, queen of the prairie extract, rose water, silica, sodium, hydroxymethyl glycinate, vegetable glycerin, witch hazel, and yucca extract. The method includes soaking an affected area in the solution for a predetermined period of time.

16 Claims, 2 Drawing Sheets

SYSTEMS AND METHODS FOR TREATING FIBROMYALGIA

RELATED APPLICATIONS

This is a continuation application of U.S. patent application Ser. No. 12/484,567, filed Jun. 15, 2009, and entitled SYSTEMS AND METHODS FOR TREATING FIBROMYALGIA, which is incorporated herein by reference in its entirety.

BACKGROUND OF THE INVENTION

1. Field of the Invention

The present invention relates to systems and methods for treating fibromyalgia in a patient. In particular, at least some embodiments of the present invention relate to systems and methods for relieving symptoms associated with fibromyalgia, including widespread aching, stiffness, fatigue, and localized points of tenderness.

2. Background and Related Art

Fibromyalgia is a syndrome characterized by chronic and intense generalized pain, or widespread chronic pain over portions of the body; the pain is not limited to muscle tissue and may also be experienced in the skin. In fibromyalgia, such generalized chronic pain is often accompanied by symptoms including fatigue, malaise, depression, anxiety, muscle tightness in the morning, muscle stiffness and sleep disorders. Other accompanying symptoms also include headaches, facial pain, cognitive impairment (memory lapses, loss of concentration), gastrointestinal complaints (visceral pain, digestive system disorders, flatulency), frequent urination, diarrhea, constipation and dysmenorrhea.

It has been reported that 3.4% of women and 0.5% of men in the U.S. general population suffer from fibromyalgia. Moreover, fibromyalgia occurs more often in women generally between 25 and 50 years of age, with women accounting for approximately 80% of all patients.

At present, the causes and mechanisms triggering the onset of fibromyalgia are not known, but are believed to include psychological factors brought on by stress or the like, viral infections, heredity, and immune and neural transmitter disorders. Fibromyalgia is a condition vastly different from many general painful conditions brought on by nociceptive stimulus, which damages or may possibly damage tissue, and no related pathological findings are observed on the pain regions.

Most anti-inflammatory analgesics such as non-steroidal anti-inflammatory drugs (NSAIDs), which are widely used for treating pain in general, are not very effective as treatment for fibromyalgia. Furthermore, various drugs including muscle relaxants, opioid analgesics and anti-anxiety agents have undergone trial use, but drug efficacy differs greatly among individuals and thus no prominent effect has been recognized. Consequently, as a current treatment of fibromyalgia, the drug therapy with anti-depressants, the combined administration of antidepressants and NSAIDs, the administration of local anesthetics or steroids to painful sites, massages, therapeutic exercise, sleep therapy and the like are merely performed. However, the curative effects of all the therapeutic agents and methods differ greatly among individuals and have not been established as methods of the treatment, partly due to the fact that the cause of fibromyalgia has yet to be determined.

As explained above, given that the causes and mechanisms triggering the onset of fibromyalgia are not clear at present, and no drug has been found to demonstrate a prominent curative effect, medical facilities are in great need of a highly safe and effective therapeutic agent. Thus, while techniques currently exist that are used to fibromyalgia, challenges still exist. Accordingly, it would be an improvement in the art to augment or even replace current techniques with other techniques.

SUMMARY OF THE INVENTION

The present invention relates to systems and methods for treating fibromyalgia in a patient. In particular, at least some embodiments of the present invention relate to systems and methods for relieving symptoms associated with fibromyalgia, including widespread aching, stiffness, fatigue, and localized points of tenderness.

Implementation of the present invention takes place in association with the use of menthol, camphor, and capsaicin as active ingredients, in combination with aloe vera extract, carbomer, decyl polyglucose, deionized water, grapefruit seed extract, green tea extract, orange peel extract, queen of the prairie extract, rose water, silica, sodium, hydroxymethyl glycinate, vegetable glycerin, witch hazel, and yucca extract to treat symptoms commonly associated with the fibromyalgia.

In at least some implementations of the present invention, the composition is in the form of a product sold under the trademark SORENOMORE™ and is used in accordance with embodiments of the present invention to treat and provide relief from symptoms associated with fibromyalgia. The SORENOMORE™ product is available from the www-.sorenomore.com website at 150 East Center Street, Moab, Utah 84532.

The SORENOMORE™ product and composition, or the combination of aforementioned ingredients, is generally effective to alleviate pain. Specifically, certain plant extracts are combined with certain active ingredients resulting in an analgesic gel that provides temporary relief to those suffering minor aches and pains. Pain relief is generally achieved by massaging the combination of ingredients onto an affected area and is especially useful for those with arthritis, backaches, strains, bruises, and sprains. The combination of ingredients further includes unique heating and cooling properties to further comfort the user.

However, in a preferred embodiment, the combination of capsaicin, camphor and menthol, as active ingredients, and Aloe Vera Extract, Carbomer, Decyl Polyglucose, Deionized Water, Grapefruit Seed Extract, Green Tea Extract, Orange Peel Extract, Queen of the Prairie Extract, Rose Water, Silica, Sodium Hydroxymethyl Glycinate, Vegetable Glycerin, Witch Hazel, and Yucca Extract as inactive ingredients, is useful in specifically providing temporary relief of pain, discomfort, and other undesirable symptoms commonly associated with fibromyalgia.

More specifically, in at least one implementation of the present invention, the composition comprises three-percent Menthol, three-percent Camphor, and 0.03% Capsaicin with Aloe Vera Extract, Carbomer, Decyl Polyglucose, Deionized Water, Grapefruit Seed Extract, Green Tea Extract, Orange Peel Extract, Queen of the Prairie Extract, Rose Water, Silica, Sodium Hydroxymethyl Glycinate, Vegetable Glycerin, Witch Hazel, and/or Yucca Extract.

In some implementations of the present invention, the composition is applied directly to the affected area of localized pain. In other implementations, the composition is added to a volume of water in which the affected area is then soaked to receive treatment, such as in a bathtub. Still, in other implementations of the present invention, the composition is regularly administered to the affected area in combination with another method of treatment, such as a muscle relaxant, an opioid analgesic, an anti-anxiety agent, an anti-depressant, an NSAID, a local anesthetic, a steroid, massages, therapeutic exercise, or sleep therapy.

In some implementations the composition is water soluble, such that the composition can be applied to an affected area and subsequently removed with water or another liquid with properties similar to water, thereby easily removing the composition. In other implementations the composition contains no waxes, oils, artificial colors or other chemicals.

While the methods and processes of the present invention have proven to be particularly useful in the area of treating symptoms of fibromyalgia, those skilled in the art will appreciate that the methods and processes of the present invention may be used in a variety of different applications and compositions to treat and provide relief from ailments associated with pain and discomfort.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

Figure 1:
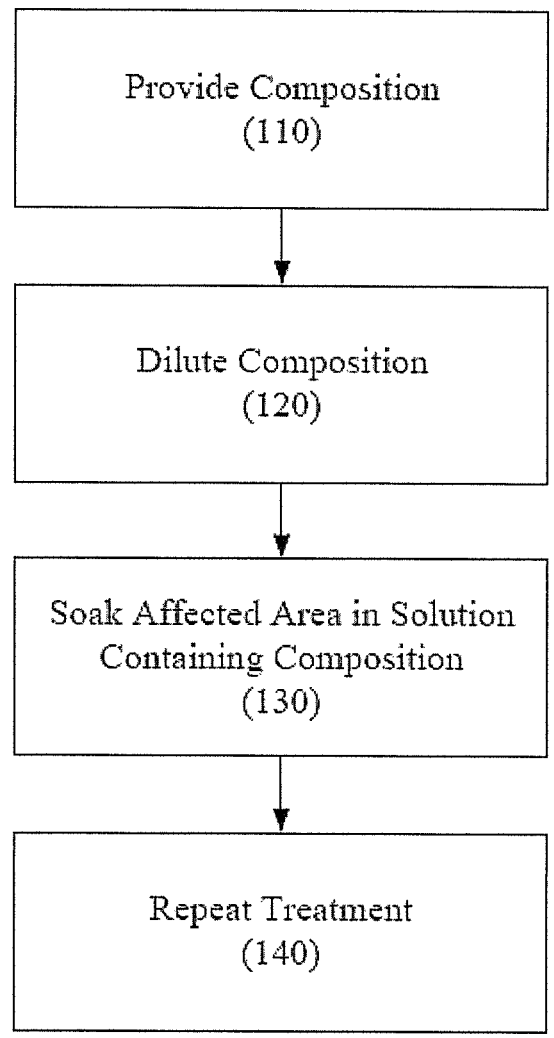
FIG. 1 is a flow chart detailing an implementation of a method for administering a composition to an affected area of a patient.

The present invention relates to systems and methods for treating fibromyalgia in a patient. In particular, at least some embodiments of the present invention relate to systems and methods for relieving symptoms associated with fibromyalgia, including widespread aching, stiffness, fatigue, and localized points of tenderness.

Embodiments of the present invention embrace the use or application of a composition having menthol, camphor, and/or capsaicin as active ingredients. In further embodiments, the one or more active ingredients are further com, in combination with aloe vera extract, carbomer, decyl polyglucose, deionized water, grapefruit seed extract, green tea extract, orange peel extract, queen of the prairie extract, rose water, silica, sodium, hydroxymethyl glycinate, vegetable glycerin, witch hazel, and yucca extract to treat and provide relief from symptoms associated with fibromyalgia.

In at least some implementations of the present invention, the composition is in the form of a product sold under the trademark SORENOMORE™ and is used in accordance with embodiments of the present invention to provide temporary relief from pains and symptoms associated with fibromyalgia. The SORENOMORE™ product is available from the www.sorenomore.com website at 150 East Center Street, Moab, Utah 84532.

The SORENOMORE™ product and composition, or the combination of aforementioned ingredients, is generally effective to alleviate pain. Specifically, certain plant extracts are combined with certain active ingredients resulting in an analgesic gel that provides temporary relief to those suffering minor aches and pains. Pain relief is generally achieved by massaging the combination of ingredients onto an affected area and is especially useful for those with arthritis, backaches, strains, bruises, and sprains. The combination of ingredients further includes unique heating and cooling properties to further comfort the user.

However, in a preferred embodiment, the combination of capsaicin, camphor and menthol, as active ingredients, and Aloe Vera Extract, Carbomer, Decyl Polyglucose, Deionized Water, Grapefruit Seed Extract, Green Tea Extract, Orange Peel Extract, Queen of the Prairie Extract, Rose Water, Silica, Sodium Hydroxymethyl Glycinate, Vegetable Glycerin, Witch Hazel, and Yucca Extract as inactive ingredients, is useful in specifically providing temporary relief of pain, discomfort, and other undesirable symptoms commonly associated with fibromyalgia.

More specifically, in at least one implementation of the present invention, the composition comprises three-percent Menthol, three-percent Camphor, and 0.03% Capsaicin with Aloe Vera Extract, Carbomer, Decyl Polyglucose, Deionized Water, Grapefruit Seed Extract, Green Tea Extract, Orange Peel Extract, Queen of the Prairie Extract, Rose Water, Silica, Sodium Hydroxymethyl Glycinate, Vegetable Glycerin, Witch Hazel, and/or Yucca Extract.

In some implementations of the present invention, the composition is applied directly to the affected area of localized pain. In other implementations, the composition is added to a volume of water in which the affected area is then soaked to receive treatment, such as in a bathtub. Still, in other implementations of the present invention, the composition is regularly administered to the affected area in combination with another method of treatment, such as a muscle relaxant, an opioid analgesic, an anti-anxiety agent, an anti-depressant, an NSAID, a local anesthetic, a steroid, massages, therapeutic exercise, or sleep therapy.

In some implementations the composition is water soluble, such that the composition can be applied to an affected area and subsequently removed with water or another liquid with properties similar to water, thereby easily removing the composition. In other implementations the composition contains no waxes, oils, artificial colors or other chemicals.

It is emphasized that the present invention, as illustrated in the figures and description herein, may be embodied in other forms. For example, the present invention may be used in conjunction with another product to treat additional symptoms of the host. In one embodiment, the composition of the present invention is used in conjunction with a moisturizing agent. In another embodiment, the composition of the present invention is used in conjunction with an exfoliant. In yet another embodiment, the composition of the present invention is used in conjunction with an antibiotic to treat secondary infections. Thus, neither the drawings nor the following, more detailed description of the various embodiments of the system and method of the present invention limit the scope of the invention. The drawings and detailed description are merely representative of examples of embodiments of the invention; the substantive scope of the present invention is limited only by the appended claims recited to describe the many embodiments. The various embodiments of the invention are best understood by reference to the drawings, wherein like elements are designated by like alphanumeric character throughout.

Figure 2:
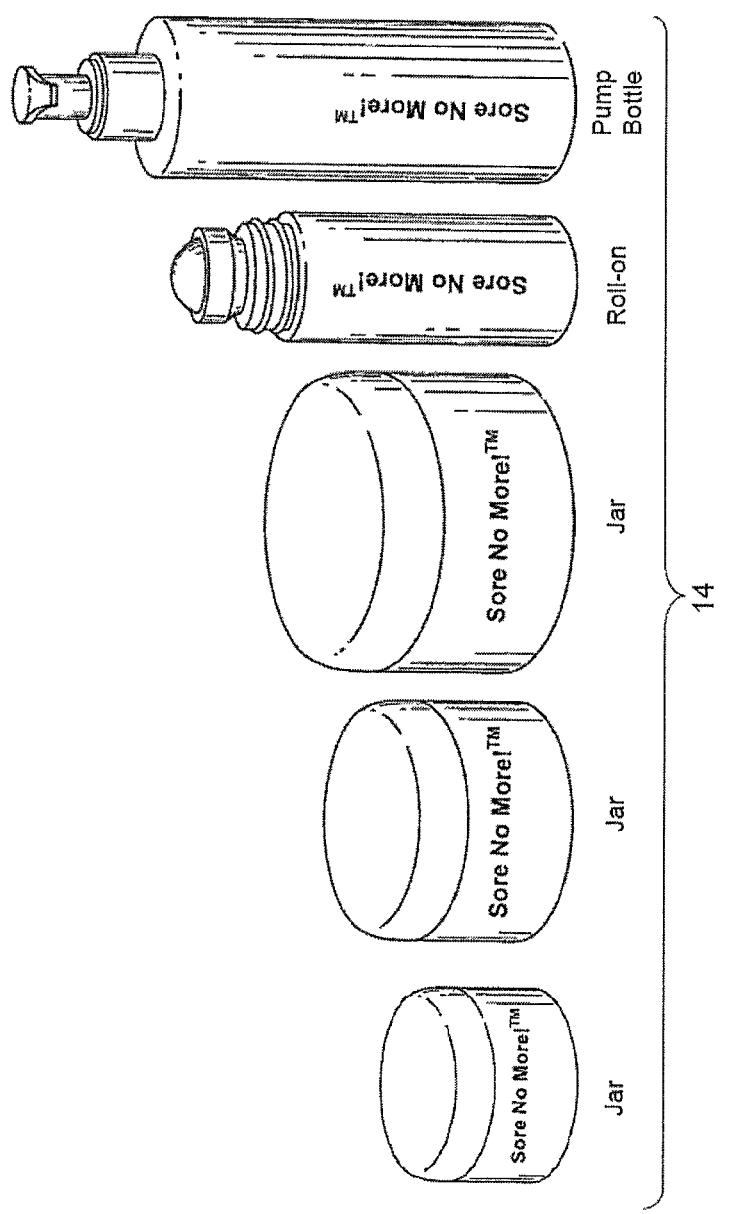
FIG. 2 is a perspective view of various products sold under the trademark SORENOMORE™.

Methods for treating symptoms of fibromyalgia generally include any method where the composition is applied directly to the affected area. However, FIG. 1 provides a flowchart detailing a method for treating fibromyalgia with the SORENOMORE™ product and composition, or a combination of the aforementioned ingredients. A first step 110 includes providing a suitable composition. As previously discussed, a suitable composition may include the SORENOMORE™ product 14, as shown in FIG. 2. The SORENOMORE™ product 14 is sold under the trademark SORENOMORE, and comprises a formulation including multiple chemical components. Specifically, the active components of the product 14 include 3% Menthol, 3% Camphor and 0.03% Capsaicin. In some implementations of the present invention the active components may further include Menthol in the range of about 0.5% v/v to about 10% v/v, Camphor in the range of about 0.5% v/v to about 10% v/v, and Capsaicin in the range of about 0.005% v/v to about 0.1% v/v. In other embodiments, the active components include at least one of Menthol, Camphor, and Capsaicin.

In some embodiments, additional components are added to the active ingredients to provide a sufficient carrier for the active ingredients. In some embodiments the carrier is water soluble. In other embodiments the carrier includes solvents and properties to readily penetrate the epithelium to provide rapid and efficient transfer of the active ingredients to the affected areas of the user. In some implementations of the present invention, the product 14 may further include one or more of the following: aloe vera extract, carbomer, grapefruit seed extract, green tea extract, orange peel extract, queen of the prairie extract, vegetable glycerin, witch hazel, yucca extract, rose water, decyl polyglucose, deionized water, silica, and sodium hydroxymethyl glycinate. General properties regarding these additional components of the composition 14 are included in Table 1.

TABLE 1

| Ingredient | Structural | Function |
|---|---|---|
| Menthol Molecular Formula: $C_{10}H_{20}O$ | | Obtained naturally from peppermint or other mint oils. It is used to give a cool feeling to the sking after application. It is also a very mild local anesthetic. |
| Camphor Molecular Formula: $C_{10}H_{16}O$ | | Derived from the wood of the camphor tree. It gives a cool feeling to the skin and works as a skin-conditioning agent Have antiseptic and anesthetic properties. |
| Capsaicin Molecular Formula: $C_{18}H_{27}NO_2$ | | A stimulant, biological product that relieves aches and pains of arthritis by intercepting the pain signals sent to the brain due to inflamed joints. |
| Aloe Vera Extract | From the leaves of one or more of species of the aloe plant. Uses include treating burns and mild abrasions and are historically a strong skin-conditioning agent. | |
| Carbomer | It is a polymer of acrylic acid. Used to control the viscosity. | |
| Decyl Polyglucose | Derived from corn and fats of coconut and palm kernel oils. It is used as a surfactant, | |
| Vegetable Glycerin | A Polyhydric alcohol used as a humectant and skin-conditioning agent. | |
| Grapefruit Seed Extract | An organic anti-microbial and fungicidal agent that is non-corrosive and non-irritant to the skin. | |
| Green Tea Extract | Biological additive used as an anti-irritant. Rich in vitamin 'C' and fluoride, acting as a mild antibacterial agent. | |
| Orange Peel Extract | An extract from the rinds of oranges citrus sinensis with the properties of an anti-inflammatoryy biological additive. | |
| Queen of the Prairie Extract | Biological antiseptic containing high levels of salicylic acid. | |
| Rose water | An aqueous solution of the odoriferous species of flowers of *rosa centifolia*. | |
| Silica | An inorganic oxide working as an opacifying agent. | |
| Sodium Hydroxymethyl | Sodium salt of the substituted amino acid for a preservative and neutralizer. | |
| Deionized water | Purified water to control viscosity. | |

TABLE 1-continued

| Ingredient | Structural | Function |
| --- | --- | --- |
| Witch hazel | An astringent obtained from *hamamelis virginiana*. | |
| Yucca Extract | A biological skin-conditioning agent derived from a select group of cactus in the Yucca family that is used to treat burns and mild abrasions by working as an anti-inflammatory agent and reducing erythema | |

Additional components of the composition, as shown in Table 1, may be added to the composition in any concentration to provide a carrier for the active ingredients having desirable physical and medicinal properties. For example, some implementations of the present invention require increased concentrations of carbomer to increase the overall viscosity of the final composition. In other embodiments, an increased volume of water is required to decrease the viscosity of the final composition. Additional components may be increased or decreased to further adjust properties of the composition, such as scent, analgesic, and antiseptic properties.

A composition comprised of ingredients found in Table 1 may be applied to an affected area of a patient to provide relief from symptoms associated with fibromyalgia. Additionally, the composition may be applied to an affected area of a patient to provide relief from pains and discomfort unrelated to fibromyalgia. In addition to the ingredients of Table 1, components may be added to the composition to obtain a desired benefit. For example, in some embodiments an additional moisturizer is added to the composition to treat dry or irritated skin of the patient. In other embodiments, an antibiotic is added to the composition to treat a secondary infection afflicting the patient. In other embodiments, an analgesic is added to the composition to further soothe the affected area of the patient. In yet other embodiments, essential oils are added to the composition to change the scent of the composition. Other embodiments further include a cleansing agent, a conditioner, an antibacterial agent, an antifungal agent, or a scent. Finally, in some embodiments, compressed, liquefied volatile gasses are added to the composition to provide an aerosol.

The composition 14 may include any beneficial combination of the abovementioned components. The composition 14 may be applied to the affected area by any necessary means. For example, in some embodiments the composition 14 is provided in the form of, but not limited to, a gel, lotion, a shampoo, a conditioner, a detergent, a foam, a spray, a powder, a balm, or any similar medium so it may be externally and topically applied to an affected area. When applied topically, the composition 14 is applied liberally and rubbed into the surface of the affected area. Generally, the composition 14 is left in place for a sufficient period of time so as to allow the composition to penetrate the epithelium. In some embodiments, the composition 14 is applied to the affected area for a period from about 30 seconds to about one hour. In other embodiments, the composition 14 is applied to the affected area for a period of time from about one minute to about fifteen minutes. Still, in other embodiments the composition 14 is applied to the affected area for a period of about 10 minutes.

The composition 14 may also be indirectly applied to the affected area to provide relief. In some embodiments the composition 14 is diluted in solvent, as shown in step 120 of FIG. 1. In this step 120 the composition 14 is added to a solvent to produce a solution in which the patient soaks the affected area. In some embodiments the composition is dissolved in an inorganic solvent, such as water. In other embodiments the composition is dissolved in an organic solvent, such as Dimethyl Sulfoxide. An appropriate solvent and dilution is selected based upon the dimensions of the affected area, as well as a required dosing. For example, where the affected area is limited to the hand of the patient, the volume and dilution of the composition is prepared to allow the patient to soak their hand in the solution. Similarly, where the affected area comprises multiple regions of the patient's body, a larger volume of solution is prepared to allow the patient to soak their entire body in the solution. For example, in some embodiments the composition 14 is diluted in bathwater to a desired concentration.

Desired concentrations of the composition 14 in the solvent may be determined by one of ordinary skill in the art. In some implementations of the present invention, a final concentration of the composition in the solution is selected within the range of about 0.001% v/v to about 0.1% v/v. In other embodiments, the final concentration of the composition 14 in the solution is selected within the range of about 0.0078% v/v to about 0.026% v/v. Yet in other embodiments of the present invention, the final concentration of the composition 14 in the solution is selected within the range of about 0.01% v/v to about 0.02% v/v. In some embodiments, one-fourth to four tablespoons of the composition 14 is dissolved in bathwater to provide a soaking solution. In other embodiments one to two tablespoons of the composition 14 is dissolved in bathwater to provide a soaking solution. Finally, in other embodiments about 2 tablespoons of the composition 14 is dissolved in bathwater to provide a soaking solution.

In some methods of the present invention, the composition is applied to the affected area via soaking the affected area in a solution, as shown in step 130 of FIG. 1. This step 130 provides sufficient exposure to the composition 14 to allow the composition 14 to effectively treat the affected area of the patient. In some embodiments the affected area of the patient is soaked in the solution within a range from about five minutes to about 2 hours. In other embodiments the affected area of the patient is soaked in the solution within a range from about forty-five minutes to about ninety minutes. Finally, in some embodiments the affected area of the patient is soaked in the solution for about one hour.

Application of the composition may be repeated to provide sustained relief, as shown in step 140 of FIG. 1. For example, in some embodiments the composition 14 is applied to the affected area up to three times within a twenty-four hour period. In other embodiments, the composition 14 is applied to the affected area at hourly intervals. Still, in other embodiments the composition 14 is applied and reapplied as needed to relieve the undesirable symptoms.

The composition 14 provides relief due to the natural anti-inflammatory and analgesic properties of the active ingredients listed above. Furthermore, the combination of active and inactive ingredients provides a composition 14 that is readily transferred through the epithelium and delivered directly to the source of the unwanted symptoms. As such, inflamed tissues and nerve receptors resultant from the conditions are quickly and efficiently treated to provide desired relief. Additionally, the water soluble nature of the composition 14 readily dissociates in water and is highly absorbed by well hydrated skin. Thus, the combination of soaking the affected area in a solution of the composition 14 in water further enhances the ability of the composition 14 to penetrate the epithelium.

Following treatment of the affected area with the composition 14, the affected area may be rinsed with an appropriate rinsing agent. For example, where the composition 14 is water soluble, the composition 14 is removed from the treated area with water, or another liquid with properties similar to water. Alternatively, the composition 14 is left in place to provide continued administration of the composition to the affected area.

Thus, as discussed herein, the embodiments of the present invention embrace compositions and methods of administration for treating symptoms associated with fibromyalgia. In particular, at least some embodiments of the present invention relate to systems and methods for providing relief locally and systemically from symptoms associated with fibromyalgia and other similarly associated discomforts.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method of treating fibromyalgia in a human in need thereof, the method comprising:
   (i) topically administering to the human in need thereof a composition consisting essentially of menthol at about 0.5% v/v to about 10% v/v, camphor at about 0.5% v/v to about 10% v/v, capsaicin at about 0.005% v/v to about 0.1% v/v, and therapeutically effective amounts of aloe vera extract, carbomer, decyl polyglucose, a grapefruit seed extract, an orange peel extract, a green tea extract, a queen of the prairie extract, rose water, a hydroxymethyl glycinate, glycerin, witch hazel, and yucca extract;
   (ii) diluting the composition in a solvent to provide a solution which has therapeutically effective amounts of the composition; and
   (iii) topically soaking an affected area of the human in need thereof in the solution for a desired period of time to effectively treat the fibromyalgia in the human.

2. The method of claim 1, wherein the composition is in the form of a gel or a lotion.

3. The method of claim 1, wherein diluting the composition provides the composition with a concentration of between about 0.001% v/v and about 0.1% v/v in the solution.

4. The method of claim 1, further comprising massaging the affected area of the human.

5. The method of claim 1, wherein the composition contains a water-soluble carrier.

6. A method for treating fibromyalgia in a human in need thereof, the method comprising:
   (i) obtaining a composition consisting essentially of menthol at a concentration in the composition of about 0.5% v/v to about 10% v/v, camphor at about 0.5% v/v to about 10% v/v, capsaicin at about 0.005% v/v to about 0.1% v/v, and therapeutically effective amounts of aloe vera extract, carbomer, decyl polyglucose, grapefruit seed extract, orange peel extract, green tea extract, queen of the prairie extract, rose water, hydroxymethyl glycinate, glycerin, witch hazel, and yucca extract;
   (ii) diluting the composition in a solvent to provide a solution which has a therapeutically effective amount of the composition; and
   (iii) topically administering an affected area of the human in need thereof with the solution for a desired period of time to effectively treat the fibromyalgia in the human in need thereof.

7. The method of claim 6, wherein the composition contains a water-soluble carrier.

8. The method of claim 6, further comprising massaging the affected area of the human.

9. The method of claim 6, wherein diluting the composition provides the composition with a concentration of between about 0.001% v/v and about 0.1% v/v in the solution.

10. The method of claim 6, wherein the topically administering the affected area with the solution comprises soaking the affected area of the human in the solution.

11. A method for treating fibromyalgia in a human in need thereof, the method comprising:
    (i) obtaining a composition consisting essentially of menthol at a concentration in the composition of about 0.5% v/v to about 10% v/v, camphor at about 0.5% v/v to about 10% v/v, capsaicin at about 0.005% v/v to about 0.1% v/v, therapeutically effective amounts of aloe vera extract, grapefruit seed extract, green tea extract, queen of the prairie extract, and yucca extract and at least one of carbomer, decyl polyglucose, orange peel extract, rose water, hydroxymethyl glycinate, glycerin, and witch hazel;
    (ii) diluting the composition in a solvent to provide a solution which has a therapeutically effective amount of the composition; and
    (iii) topically administering an affected area of the human in need thereof with the solution for a desired period of time to effectively treat the fibromyalgia in the human in need thereof.

12. The method of claim 11, wherein the composition is in the form of a gel.

13. The method of claim 11, wherein diluting the composition provides the composition with a concentration of between about 0.001% v/v and about 0.1% v/v in the solution.

14. The method of claim 11, further comprising massaging the affected area of the human.

15. The method of claim 11, wherein the composition contains a carrier that is water-soluble.

16. The method of claim 11, wherein topically administering the affected area with the solution comprises soaking the affected area of the human in the solution.

* * * * *